(12) United States Patent
Budolfsen et al.

(10) Patent No.: US 6,413,560 B1
(45) Date of Patent: *Jul. 2, 2002

(54) METHOD FOR REDUCING SYNERESIS

(75) Inventors: Gitte Budolfsen, Frederiksberg; Mette Ohrstrom Jensen, Snekkersten; Anne Glud Rasmussen, Copenhagen, all of (DK)

(73) Assignee: Novozymes A/S, Bagsvaerd (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/013,673

(22) Filed: Jan. 26, 1998

Related U.S. Application Data

(63) Continuation of application No. PCT/DK96/00392, filed on Sep. 18, 1996.

(30) Foreign Application Priority Data

Sep. 22, 1995 (DK) .............................................. 1062/95

(51) Int. Cl.⁷ ................................................. A23L 1/05
(52) U.S. Cl. ............................ 426/50; 426/49; 426/52; 426/577
(58) Field of Search .............................. 426/49, 50, 51, 426/52, 573, 577

(56) References Cited

U.S. PATENT DOCUMENTS

| 2,373,729 A | 4/1945 | Willaman |
| 2,534,263 A | 12/1950 | Hills |
| 4,200,694 A | 4/1980 | Ishii et al. |

FOREIGN PATENT DOCUMENTS

| EP | 0 388 593 | 9/1990 |
| GB | 1 508 993 | 4/1978 |
| GB | 1 525 123 | 9/1978 |
| WO | 93/09683 | 5/1993 |
| WO | 94/12055 | 6/1994 |

OTHER PUBLICATIONS

Flores et al, AN 85(03):H0053 FSTA, abstracting Flussiges Obst, 51 (7) 320–324 and 327–328, 1984.*
Bock et al, AN 72(02):J0211 FSTA, abstracting Ernahrungs-forschung, 15(4) 403–415, 1970.*
Grampp, E., AN 73(02):J0297 FSTA, abstracting Dechema--Monographien, 70, 175–186, 1972.*
Grampp, E., AN 77:112664 CA, abstracting Dechema--Monogr., 70, 175–186, 1972.*
Kitsukoo Shiyokuhin Kogyo K.K., Japanese Abstract of JP 59–25673, 2/84.
Kitsukoo Shiyokuhin Kogyo K.K., Japanese Abstract of JP 59–25674, 2/84.
Calesnick et al., Eastern Reg. Res. Lab., PA, pp. 432–440, (Aug. 9, 1950).
Meurens, revue Des Fermentations, vol. 33, No. 4, pp. 95–104 (1978).
Speirs et al., J. Sci. Food Agric., vol. 31, pp. 1287–1294, (1980).
King et al., J. Sci. Food Agric., vol. 45, pp. 231–241 (1988).

* cited by examiner

*Primary Examiner*—Leslie Wong
(74) *Attorney, Agent, or Firm*—Elias Lambiris; Jason Garbell

(57) ABSTRACT

The present invention relates to methods for reducing the serum separation of an aqueous mass containing pectin, including the steps of: (a) providing an aqueous mass substantially free from pectin depolymerizing enzymes, (b) adding an effective amount of pectinesterase, preferably substantially free from pectin depolymerizing enzymes, and (c) incubating said mass in the presence of divalent cations, is disclosed. The method has been found to be advantageous with products wherein the pectin containing aqueous mass is derived from broccoli, pepper, mustard, apples, tomatoes oranges, lemons, grapes, lime, pears, carrots, peas, cauliflower, and berries, such as blackcurrant, blue-berries, strawberries, and raspberries to obtain products, such as jam, marmalade, jelly, juice, paste, soup, dressing, sauce, condiment, ketchup, salsa, chutney, pudding, mousse, or other deserts.

15 Claims, No Drawings

METHOD FOR REDUCING SYNERESIS

CROSS-REFERENCE TO RELATED APPLICATIONS

This application is a continuation of application serial. No. PCT/DK96/00392 filed Sep. 18, 1996 and claims priority under 35 U.S.C. 119 of Danish application serial no. 1062/95 filed Sep. 22, 1995, the contents of which are fully incorporated herein by reference.

FIELD OF THE INVENTION

The present invention relates to a method for reducing the serum separation/syneresis in a pectin containing aqueous mass by the use of certain enzymes, and enzyme compositions therefore.

BACKGROUND OF THE INVENTION

Dicotyledonous plants comprise some of the major crops cultured by man, such as beans, peas, beets as well as most other fruits and vegetables.

The primary cell wall and middle lamella of these plants usually have a high content of pectic substances. The pectic matrix consists of smooth regions of polygalacturonic acids and of rhamnogalacturonan.

The polygalacturonic acid areas are usually highly esterified by methoxyl groups. Side groups consisting of araban, galactan and arabinogalactan are attached to the rhamnogalacturonan residues. The presence and distribution of the carboxy-methyl groups in pectin significantly alters its solubility and physico-chemical and gel forming properties.

This is of major importance both in the plant cell wall, where the pectic matrix is a key regulator of porosity and passive diffusion of macromolecules but also in industrial processing of pectin and pectin containing plant material.

Pectinesterase (PE), EC 3.1.1.11 (*Enzyme Nomenclature* 1992, Academic Press, Inc., 1992), hydrolyses the ester linkage between methanol and galacturonic acid in esterified pectin. PE is found both in plants and in microorganisms. That is, PE offers a possibility of completely controlling the properties of pectin by altering the degree of esterification (DE).

Thus, an endogenous highly methoxylated content of pectin (HM pectin) in various fruits and vegetables can enzymatically be modified to a low methoxylated pectin by pectinesterase. In combination with the natural content of calcium ions this is sufficient for an in situ gelation or an in situ thickening to take place if the PE is substantially free from depolymerizing enzyme activities (Calesnik, E. J. et al 1950, *Arch. of Biochem.*, 29, 432–440. Meurens, M., 1978, Rev. *Ferment. Ind. Aliment.*, 33, 95–104), since the presence of such activities will substantially break down the pectin.

It is a well known problem that several products that are fully or partially vegetable or fruit based, such as ketchup, mustard and jam, "weep" or separate on standing. The processes used result in an indelicate appearance of the product. Furthermore use of the product on e.g. bread or rolls results in the bread or roll getting soaked and disintegrate. Similarly other products such as fruit soups and yoghurts separate and develop an unattractive appearance.

It is an object of this invention to provide a method of causing a decrease of the serum separation in an aqueous mass containing methoxylated pectin without the need for addition of stabilising agents, such as externally added hydrocolloids, modified starch etc.

SUMMARY OF THE INVENTION

The present invention relates to a method for reducing the serum separation of an aqueous mass containing pectin, comprising the steps of
(a) providing an aqueous mass substantially free from pectin depolymerizing enzymes.
(b) adding an effective amount of pectinesterase, and
(c) incubating said mass in the presence of divalent cations.

Surprisingly it has been found that no other stabilising agent is needed in relation to the method according to the invention.

Hereby the method according to the invention offers the unique feature that the serum separation can be reduced or even avoided without the addition of any further external agents, whereby the only external agent being added is an effective amount of pectinesterase, and optionally divalent ions, such as alkaline earth ions, especially calcium ions.

Thus, for the first time it has been proven possible to utilise deesterified endogenous pectin in itself for a direct reduction of serum separation.

DETAILED DESCRIPTION OF THE INVENTION

As indicated the present invention relates to a method for reducing the serum separation of an aqueous mass containing pectin, comprising the steps of:
(a) providing an aqueous mass substantially free from pectin depolymerizing enzymes.
(b) adding an effective amount of pectinesterase, and
(c) incubating said mass in the presence of divalent cations.

According to one embodiment of the invention the pectin may be endogenous HM.

In an embodiment of the method according to the invention the pectinesterase used is derived from a fungus of the genus Aspergillus, preferably *A. japonicus*, (S. Ishii et al., 1979, *Journal of Food Science* 44, p 611–614), *A. aculeatus*, *A. niger* (EP 0 388 593 A1), *A. awamori* (EP 0 388 593 A1), or the genera Fusarium, Sclerotonia, or Penicillium, (Kikkoman: DE 2843351; U.S. Pat. No. 4,200, 694). These pectinesterases exhibit a relatively low pH optimum, corresponding to the relatively low pH optimum of many fruits.

The pectinesterase to be used in the invention should preferably be substantially free from pectin depolymerizing enzymes, such as pectinlyases or polygalacturonases. In case these activities are present in substantial amounts the pectin will be degraded.

Such enzymes are obtainable by using a host system for the expression of the enzyme which does not produce any pectin depolymerizing enzymes (WO 94/25575).

The activity of the pectinesterase is indicated in Pectin Esterase Units (PEU) defined as the amount of enzyme which under standardised conditions hydrolyses 1 mmol carboxyl groups per minute. A folder describing the Novo Nordisk assay ABT-SM-0005.02.1 is available upon request.

According to the invention the pectin should be present in the aqueous mass in an amount from 0.1% w/w to 10% w/w preferably from 0.2% w/w to 1.0% w/w.

In further embodiments of the invention it may be advantageous to add sugar, acetic acid and/or salt in amounts from 0–60% w/w, 0–10% w/w, and 0–10% w/w, respectively.

The method of the invention will normally be carried out at a pH value from 2.5 to 7.5, preferably from pH 3 to pH 5, and for a time period for the incubation step from 5 to 60 minutes, preferably from 10 seconds to 30 minutes.

The incubation step will normally be performed at a temperature from 10 to 60° C., preferably from 15 to 50° C.

According to the invention the PE is added in an amount of from 4 to 400 PEU, preferably from 9 to 135 PEU, better from 25 to 110 PEU, still better from 35 to 90 PEU, and more preferably from 45 to 70 PEU/kg VSS (Vegetable Soluble Solids, VSS is measured refractometrically as % Brix).

According to the invention the method is designed for use with a pertinacious mass, especially food, and especially products such as tomato juice, tomato slurry, tomato paste or salsa or ketchup.

The method of the invention has been found to be advantageous with products wherein the pectin containing aqueous mass is derived from broccoli, pepper, mustard, apples, tomatoes oranges, lemons, grapes, lime, pears, carrots, peas, cauliflower, and berries, such as blackcurrant, blue-berries, strawberries, and raspberries.

Products obtained by the process of the invention are such as jam, marmalade, jelly, juice, paste, soup, dressing, sauce, condiment, ketchup, salsa, chutney, pudding, mousse, or other deserts.

MATERIALS AND METHODS

Materials:
  Hot break tomato paste
  Pectinesterase prepared according to WO 94/25575
  Brookfield Viscometer, DVII
  DUR Refractometer, Schmidt and Haensch, Germany
  Blotter test paper (Bridge & Company)
Methods:
  Viscosity Measurement:
  The viscosity was measured by Spindel C, specification no. 93. Measurements at shear rate 2.5 rpm and 20 rpm were carried out.
  Measurement of Vegetable Soluble Solids (VSS):
  A drop of the test solution is applied to the sample well in the DUR refractometer.
  The instrument indicates directly the solids content in % Brix.
  Blotter Test:
  To quantify the serum separation from the solid content the serum separation evaluation procedure of using a blotter test paper was used (Gould W.A., et al 1992, Tomato Production Processing & Technology 3rd edition CTI Publications).
  5 7.0 g of ketchup was weighted out in a metal cylinder (dia 38 mm) placed in the centre of the blotter paper. After 7 min the serum separation was measured at the four rules. The measurement is given as an average of the four figures.
  A low value indicates a low degree of syneresis/serum separation.

EXAMPLES

Example 1

Hot break tomato paste was diluted from 22.5% VSS to 8.5% VSS and homogenised at 300 bar. Afterwards, eight samples of 455 g were weighed out in 1000 ml containers, the temperature was adjusted to 40° C.

8×25 ml enzyme solutions of increasing PE concentrations were added to the above mentioned substrates, the final enzyme protein concentrations were as follows: 0, 17, 34, 59, 68, 85, 102, 136 PEU/kg VSS. The samples were then incubated for 30 min at 40° C.

After the enzyme treatment a ketchup was prepared by adding 300 g of brine to each of the samples. The brine consists of sugar, salt and acetic acid (Skott, W. P. *Die Industrielle Obst- und Gemüseverwertung*, 1970 55 229–234). The prepared ketchup were then heat treated, 88° C. in 3 min. The samples were then cooled in an ice bath and finally placed in the refrigerator until analysis could take place.

The results from the analysis is shown in Table I

TABLE I

| Pectinesterase Concentration PEU/kg VSS | Blotter Test mm | Viscosity 2.5 rpm cP | Viscosity 20 rpm cP |
|---|---|---|---|
| 0 | 20.7 | 8305 | 1455 |
| 17 | 18.2 | 9027 | 1543 |
| 34 | 14.4 | 9527 | 1660 |
| 59 | 9.7 | 8745 | 1595 |
| 68 | 5.8 | 22900 | 3330 |
| 85 | 10.3 | 31965 | 4250 |
| 102 | 14.2 | 35505 | 4780 |
| 136 | 25.0 | 45415 | 8340 |

From the Blotter test results it is clearly seen that the syneresis or serum separation can be controlled by adjusting the concentration of pectinesterase. Not surprisingly, also the viscosity depends on the enzyme concentration. It is noticed that it is possible at the same time to obtain both a reduction of the syneresis and a viscosity increase.

REFERENCES CITED IN THE SPECIFICATION

1. Calesnik, E. J. et al. 1950, *Arch. of Biochem.*, 29 432–440.
2. Meurens, M., 1978, Rev. *Ferment. Ind. Aliment.*, 33 95–104)
3. Gould W. A., et al. 1992, *Tomato Production Processing & Technology*, 3rd edition CTI Publications
4. S. Ishii et al., 1979, *Journal of Food Science* 44 611–614
5. EP 0 388 593 A1
6. DE 2843351
7. U.S. Pat. No. 4,200,694
8. WO 94/25575
9. Skott, W. P. *Die Industrielle Obst- und Gemüseverwertung*, 1970 55 229–234
10. *Enzyme Nomenclature* 1992, Academic Press, Inc., 1992
11. Novo Nordisk assay ABT-SM-0005.02.1

What is claimed is:

1. A method for preparing a pectin-containing food, said method comprising treating a food mass with pectinesterase in an amount between 17 and 102 PEU/kg VSS, wherein said treating is performed under conditions which result in (i) a reduction in syneresis of said treated mass relative to an untreated mass; (ii) an increase in viscosity of said treated mass relative to an untreated mass; and (iii) a lack of pectin depolymerization.

2. A method as defined in claim 1, further comprising adding divalent cations to said mass prior to or during said treating step.

3. A method as defined in claim 1, wherein said pectin comprises endogenous HM pectin.

4. A method as defined in claim 1, wherein said pectinesterase is derived from a fungus.

5. A method as defined in claim 1, wherein said mass is derived from broccoli, pepper, mustard, apples, tomatoes, oranges, lemons, grapes, lime, pears, carrots, peas, cauliflower, or berries.

6. A method as defined in claim 5, wherein said mass comprises tomato juice, tomato slurry, tomato paste, salsa, or ketchup.

7. A method as defined in claim 1, wherein said amount of pectinesterase is between 40 and 95 PEU/kg VSS.

8. A method as defined in claim 7, wherein said amount of pectinesterase is between 55 and 80 PEU/kg VSS.

9. A method as defined in claim 1, wherein the concentration of pectin in said mass is from 0.1% w/w to 10 % w/w.

10. A method as defined in claim 1, further comprising adding (i) sugar in an amount between 0–60% w/w; (ii) acetic acid in an amount between 0–10% w/w; (iii) salt in an amount between 0–10% w/w; or (iv) combinations of any of the foregoing.

11. A method as defined in claim 1, wherein the pH of said mass is between 2.5 and 7.5.

12. A method as defined in claim 1, wherein said contacting is performed for a time between 5 and 60 minutes.

13. A method as defined in claim 1, wherein said contacting is performed at a temperature between 10 and 60° C.

14. The method of claim 1, wherein the food product is selected from the group consisting of jam, marmalade, jelly, juice, paste, soup, dressing, sauce, condiment, ketchup, mustard, salsa, chutney, pudding, and mousse.

15. A method for preparing a pectin-containing food, said method comprising treating a food mass with pectinesterase (PE) in an amount between 17 and 102 PEU/kg VSS, wherein said pectinesterase is produced in a recombinant cell which comprises heterologous pectinesterase-encoding DNA and which does not produce pectin-depolymerizing enzymes, and wherein said treating is performed under conditions which result in (i) a reduction in syneresis of said treated mass relative to an untreated mass; (ii) an increase in viscosity of said treated mass relative to an untreated mass; and (iii) a lack of pectin depolymerization.

\* \* \* \* \*